United States Patent [19]

Gambhir

[11] Patent Number: 5,854,270
[45] Date of Patent: Dec. 29, 1998

[54] ORAL COMPOSITIONS CONTAINING ONDANSETRON

[75] Inventor: Renu Gambhir, Mississauga, Canada

[73] Assignee: Glaxo Wellcome Inc., Mississauga, Canada

[21] Appl. No.: 817,831

[22] PCT Filed: Nov. 20, 1995

[86] PCT No.: PCT/IB95/01152

§ 371 Date: Jul. 9, 1997

§ 102(e) Date: Jul. 9, 1997

[87] PCT Pub. No.: WO96/15786

PCT Pub. Date: May 30, 1996

[30] Foreign Application Priority Data

Nov. 22, 1994 [GB] United Kingdom .................. 9423588

[51] Int. Cl.$^6$ .................................................. A61K 31/415
[52] U.S. Cl. .......................................................... 514/397
[58] Field of Search ............................................. 514/397

[56] References Cited

FOREIGN PATENT DOCUMENTS

| | | |
|---|---|---|
| 0 450 757 | 10/1991 | European Pat. Off. . |
| 2 153 821 | 8/1985 | United Kingdom . |
| 94 13284 | 6/1994 | WIPO . |

OTHER PUBLICATIONS

Dittert, Sprowls' American Pharmacy, 7th Edition, pp. 84–85 (1974).

*Primary Examiner*—Raymond Henley, III
*Attorney, Agent, or Firm*—Bacon & Thomas, PLLC

[57] ABSTRACT

The invention relates to a liquid composition for oral administration comprising ondansetron or a pharmaceutically acceptable derivative thereof, a sweetener and one or more pharmaceutically acceptable excipients. The sweetener comprises one or more polyhydric alcohols and the pH of the combination lies in the range 2.0 to 5.0. Methods for the manufacture of such compositions and for their use in the treatment of conditions mediated through the action of 5-hydroxytryptamine (5 HT) at 5 $HT_3$ receptors are also included.

12 Claims, No Drawings

ORAL COMPOSITIONS CONTAINING ONDANSETRON

This application is a 371 of PCT/IB95/01152 filed Nov. 20, 1995. The present invention relates to a pharmaceutical composition containing, as active ingredient, 1,2,3,9-tetrahydro-9-methyl-3-[(2-methyl-1H-imidazol-1-yl)-methyl]-4H-carbazol4-one, in particular a liquid composition for oral administration.

In UK Patent No. 2153821B we disclose, inter alia, 1,2,3,9-tetrahydro-9-methyl-3-[(2-methyl-1H-imidazol-1-yl)methyl]-4H-carbazol-4-one, now known as ondansetron, which may be represented by the formula (I)

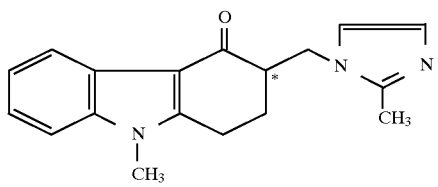

and physiologically acceptable salts, solvates and physiologically acceptable equivalents thereof.

In the aforementioned specification the compounds are described as potent and selective antagonists of 5-hydroxytryptamine (5 HT) at 'neuronal' 5 HT receptors of the type located on terminals of primary afferent nerves, and which are also present in the central nervous system. Receptors of this type are now designated 5 $HT_3$ receptors. The compounds are described as being of use in the treatment of a human or animal subject suffering from a condition caused by a disturbance of neuronal 5 HT function, for example in the treatment of migraine pain or a psychotic disorder such as schizophrenia. It is also stated that the compounds may be useful in the treatment of conditions such as anxiety, obesity and mania.

According to our European Patent Application publication No. 226266, the compounds have also been found to be anti-emetics, and may be used in the treatment or prevention of nausea and vomiting. The use of these compounds for the treatment of emesis is also described in European Patent No. 201165, which additionally refers to the use of the compounds for the treatment of irritable bowel syndrome.

Numerous clinical studies have demonstrated the effectiveness of ondansetron for the treatment of emesis, particularly the nausea and vomiting associated with cancer chemotherapy and radiotherapy and that occurring post-operatively. Hitherto, the drug has always been administered either by injection or orally.

Oral administration in the form of a conventional tablet, pill or capsule constitutes the generally preferred route for administration of pharmaceuticals since this route is generally convenient and acceptable to patients. Unfortunately such compositions may be associated with certain disadvantages, particularly in the treatment of paediatric or geriatric patients, who may dislike or have difficulty in swallowing such compositions, or where administration of a conventional tablet, pill or capsule is not feasible. It is highly desirable, particularly in the treatment of acute conditions, that pharmaceutical compositions have a rapid and consistent onset of action combined with sustained activity and good bioavailability. Rapid absorption can be achieved by parenteral injection but this is unacceptable to some patients, particularly if the drug is to be administered without direct medical supervision, i.e. self-administered.

Alternative routes for administration of ondansetron are proposed in GB 2153821, including liquid formulations for oral administration. GB 2153821 discloses a number of pharmaceutical formulations containing ondansetron, in the form of its hydrochloride dihydrate, and sucrose and sucrose-free syrup formulations for oral administration containing ondansetron hydrochloride dihydrate are specifically disclosed therein.

The present invention provides a particularly advantageous pharmaceutical composition, not hitherto specifically disclosed, which is a liquid composition of ondansetron suitable for oral administration.

The present invention therefore provides in a first aspect a liquid composition for oral administration comprising ondansetron or a pharmaceutically acceptable derivative thereof, a sweetener and one or more pharmaceutically acceptable excipients, characterised in that the sweetener comprises one or more polyhydric alcohols and the pH of the composition lies in the range 2.0 to 5.0.

By pharmaceutically acceptable derivative is meant any pharmaceutically acceptable salt or solvate of ondansetron, or any other compound, which upon administration to the recipient is capable of providing (directly or indirectly) ondansetron or an active metabolite or residue thereof.

Preferably the compositions according to the invention comprise ondansetron in the form of its hydrochloride, more particularly its hydrochloride dihydrate.

It will be appreciated by those skilled in the art that ondansetron contains one chiral centre (shown by * in the formula (I)) and that ondansetron therefore exists in the form of optical isomers (i.e. enantiomers). The invention includes all isomers of ondansetron and its pharmaceutically acceptable derivatives, including all tautomeric and optical forms, and mixtures thereof, including racemic mixtures.

Unlike the prior art compositions, the sweetener of the compositions according to the invention comprises one or more polyhydric alcohols. The applicants have found that the use of one or more polyhydric alcohols provides a surprisingly advantageous pharmaceutical composition by virtue of its good stability and acceptable taste.

It will be appreciated by those skilled in the art that the polyhydric alcohols referred to above will be the pharmaceutically acceptable polyhydric alcohols or mixtures thereof, for example sorbitol, mannitol, xylitol and maltitol. Preferably, the sweetener for use according to the invention comprises sorbitol; more preferably, the sweetener is sorbitol and xylitol; most preferably the sweetener is sorbitol.

The total polyhydric alcohol content of the liquid composition, expressed in terms of polyhydric alcohol solids, conveniently lies in the range of 20 to 85% w/v (weight by volume), such as 30 to 70% w/v, preferably 35 to 50% w/v, for example about 40% w/v.

Each polyhydric alcohol may be used in solid form or in the form of a solution. Preferably it is used in the form of a solution, such as an aqueous solution. For example sorbitol is conveniently used in the form of an aqueous solution, which is characterised in that the concentration of solids in the solution lies in the range of 64 to 72% w/w (weight by weight).

The concentration of ondansetron in the liquid composition, expressed as free base, is conveniently in the range of 0.005 to 1% w/v, such as 0.01 to 0.5% w/v, preferably 0.02 to 0.2% w/v, for example about 0.08% w/v.

The pH of liquid compositions according to the invention conveniently lies within the range 2.5 to 4.5, such as 3.0 to 4.0, for example about 3.5.

The compositions according to the invention may be in the form of liquids, suspensions or syrups. Preferably the compositions are formulated as liquids.

Conventional excipients which may be employed in the compositions according to the invention include preservatives, buffering systems, viscosity enhancing agents, flavouring aids, colouring aids, additional sweeteners, and mixtures thereof.

Suitable preservatives include one or more alkyl hydroxybenzoates such as methyl, ethyl, propyl and/or butyl hydroxybenzoates; sorbic acid or a salt thereof; benzoic acid or a salt thereof; and mixtures thereof. Preferably the compositions according to the invention comprise sodium benzoate.

Suitable buffering systems include combinations of citric acid and salts and solvates thereof, for example citric acid (anhydrous or monohydrate) combined with sodium citrate dihydrate. Preferably compositions according to the invention comprise the buffering system anhydrous citric acid and sodium citrate dihydrate.

Suitable viscosity enhancing agents include gums (e.g. Xanthan gum); glycerol; polyvinyl alcohol; polyvinylpyrrolidine; cellulose derivatives, such as carboxymethylcellulose or a salt thereof, $C_{1-4}$alkyl and/or hydroxy $C_{2-4}$alkyl ether of cellulose, such as methylcellulose, ethylcellulose, hydroxyethylcellulose, hydroxypropylcellulose, hydroxyethylmethylcellulose and hydroxypropyl-methylcellulose; and mixtures thereof.

Liquid compositions according to the invention conveniently have a viscosity which lies in the range 1 to 100 cps, such as 10 to 75 cps, for example about 15 to 50 cps.

Suitable flavouring aids include strawberry, cherry and grape flavouring aids, in particular strawberry flavouring aid.

Suitable additional sweeteners include, for example, sugars such as glucose; and cyclamate and salts thereof. Preferably compositions according to the invention are substantially free of fructose or a fructose containing sacharide (e.g. sucrose), for example containing less than 5% w/v of the fructose unit, such as less than 1% w/v of the fructose unit.

In a further preferred aspect, the invention provides a liquid composition for oral administration comprising ondansetron hydrochloride dihydrate and sorbitol.

In a yet further preferred aspect, the invention provides a liquid composition for oral administration comprising ondansetron hydrochloride dihydrate, sorbitol, sodium benzoate, anhydrous citric acid, sodium citrate dihydrate and strawberry flavouring aid.

Within the above further preferred aspects of the invention, a liquid composition having a concentration of ondansetron, expressed as the free base, of 0.02 to 0.2% w/v, for example about 0.08% w/v; a sorbitol content, expressed in terms of sorbitol solids, of 30 to 50% w/v, for example about 40% w/v; and a pH of 3.0 to 4.0, such as about 3.5, is especially preferred.

The liquid compositions for oral administration are conveniently prepared in conventional manner, for example by mixing an aqueous solution of the sweetener with an aqueous slurry of the ondansetron hydrochloride dihydrate and the excipients.

A further aspect of the invention provides a method of treating a mammal, including man, suffering from a condition mediated through the action of 5-HT at 5 $HT_3$ receptors, which comprises administration of a liquid composition for oral administration comprising ondansetron or a pharmaceutically acceptable derivative thereof, a sweetener and one or more pharmaceutically acceptable carriers or excipients, characterised in that the sweetener comprises one or more polyhydric alcohols and the pH of the composition lies in the range 2.0 to 5.0. It will be appreciated that reference to treatment is intended to include prophylaxis as well as the alleviation of established symptoms.

Conditions mediated through the action of 5 HT at 5 $HT_3$ receptors include emesis; cognitive disorders such as dementia, particularly degenerative dementia (including senile dementia, Alzheimer's disease, Pick's disease, Huntington's chorea, Parkinson's disease and Creutzfeldt-Jakob disease), and vascular dementia (including multi-infarct dementia), as well as dementia associated with intracranial space occupying lesions, trauma, infections and related conditions (including HIV infection), metabolism, toxins, anoxia and vitamin deficiency; and mild cognitive impairment associated with ageing, particularly Age Associated Memory Impairment; psychotic disorders, such as schizophrenia and mania; anxiety disorders, including panic disorder, agoraphobia, social phobia, simple phobia, obsessive compulsive disorders, post traumatic stress disorder, mixed anxiety and depression, and generalised anxiety disorder; irritable bowel syndrome and dependency on drugs and substances of abuse. Other conditions mediated in this manner include pruritis, particularly that induced by cholestasis; gastric stasis; symptoms of gastrointestinal dysfunction such as occur with peptic ulcer, reflux oesophagitis, flatulence and dyspepsia; migraine; obesity and conditions such as bulimia; pain; and depression.

Emesis, i.e. nausea, retching and vomiting, includes acute emesis, delayed emesis and anticipatory emesis. Ondansetron is useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer, poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; postoperative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastrooesophageal reflux disease, acid indigestion, overindulgence of food or drink, acid stomach, sour stomach, waterbrash/regurgitation, heartburn, such as episodic heartburn, nocturnal heartburn, and meal-induced heartburn and dyspepsia.

The pharmaceutical compositions according to the invention have particular utility for the treatment of emesis, particularly that associated with cancer chemotherapy and radiotherapy, but also that occurring post-operatively.

It will be appreciated that the precise therapeutic dose of the active ingredient will depend on the age and condition of the patient and the nature of the condition to be treated and will be at the ultimate discretion of the attendant physician.

However, in general, effective doses for the treatment of conditions mediated through the action of 5-HT at 5 $HT_3$ receptors, for example emesis, will lie in the range of 0.05 to 100 mg, such as 0.1 to 50 mg, preferably 0.5 to 25 mg, for example 1, 2, 4 or 8 mg of the active ingredient per unit dose, which could be administered in single or divided doses, for example, 1 to 4 times per day.

The volume of a unit dose of the liquid composition conveniently lies in the range of 1 to 15 ml, such as 2.5 to 10 ml, for example about 5 ml.

The following non-limiting examples further illustrate the invention.

EXAMPLE 1

|  | mg/5 ml | % w/v |
|---|---|---|
| Ondansetron HCl.2H$_2$O | 5.0[1] | 0.10 |
| Sorbitol solution (USP, EP) | 3000.0[2,3] | 60.00 |
| Citric acid anhydrous (USP, EP) | 25.0 | 0.50 |
| Sodium citrate dihydrate (USP, EP) | 7.5 | 0.15 |
| Sodium benzoate (USP, EP) | 10.0 | 0.20 |
| Strawberry flavouring | 15.0 | 0.30 |
| Purified water, qs to | 5 ml | 100.00% |

[1] equivalent to 4 mg ondansetron, as free base
[2] equivalent to 2.33 ml
[3] equivalent to: 38.4% w/v sorbitol solids, USP
40.8 to 43.2 w/v sorbitol solids, EP The sorbitol solution was mixed with water and the anhydrous citric acid added to the mixture. Water was added to the ondansetron hydrochloride dihydrate to form an aqueous slurry and the slurry was added to the mixture, followed by the sodium citrate dihydrate. The sodium benzoate was dissolved in water and the solution added to the mixture, followed by the strawberry flavouring. The mixture was made up to volume with water, filtered and filled into bottles.

EXAMPLE 2

A composition containing 2.5 mg ondansetron hydrochloride dihydrate (2 mg ondansetron, as free base) in 5 ml was prepared as described above in Example 1.

EXAMPLE 3

|  | mg/5 ml | % w/v |
|---|---|---|
| Ondansetron HCl.2H$_2$O | 5.0[1] | 0.10 |
| Xylitol (USP) | 3000.0 | 60.00 |
| Sorbitol solution (USP) | 500.0[2] | 10.00 |
| Citric acid anhydrous (USP) | 25.0 | 0.50 |
| Sodium citrate dihydrate (USP) | 7.5 | 0.15 |
| Sodium benzoate (USP) | 10.0 | 0.20 |
| Strawberry flavouring | 15.0 | 0.30 |
| Purified water, qs to | 5 ml | 100.00% |

[1] equivalent to 4 mg ondansetron, as free base
[2] equivalent to 0.39 ml

The anhydrous citric acid was dissolved in water and then the ondansetron hydrochloride dihydrate added, followed by the sodium citrate. The sodium benzoate was dissolved in water and the solution added to the mixture. Xylitol was added to the mixture, then the sorbitol solution and finally the strawberry flavouring. The mixture was made up to volume with water, filtered and filled into bottles.

EXAMPLES 4 and 5

Compositions containing 1.25 and 10 mg ondansetron hydrochloride dihydrate (1 and 8 mg ondansetron, as free base, respectively) in 5 ml are prepared as described above in Example 1.

I claim:

1. A liquid composition for oral administration comprising ondansetron or a pharmaceutically acceptable derivative thereof, a sweetener and one or more pharmaceutically acceptable excipients, characterised in that the sweetener comprises sorbitol and the pH of the composition lies in the range 2.0 to 5.0.

2. A composition according to claim 1 comprising ondansetron in the form of its hydrochloride.

3. A composition according to claim 1 comprising ondansetron in the form of its hydrochloride dihydrate.

4. A composition according to claim 1 wherein ondansetron is in the form of its hydrochloride dihydrate and the sweetener is sorbitol.

5. A composition according claim 1 wherein the concentration of ondansetron in the composition, expressed as free base, lies in the range of 0.005 to 1% w/v.

6. A composition according to claim 1 wherein the total sorbitol content of the composition, expressed in terms of sorbitol solids, lies in the range of 20 to 85% w/v.

7. A composition according to claim 1 wherein the pH lies within the range 2.5 to 4.5.

8. A composition according to claim 1 wherein the concentration of ondansetron in the composition, expressed as free base, lies in the range of 0.02 to 0.2% w/v; the total sorbitol content of the composition, expressed in terms of sorbitol solids, lies in the range of 30 to 50% w/v; and the pH lies within the range 3.0 to 4.0.

9. A composition according to claim 1 having a viscosity which lies in the range 1 to 100 cps.

10. A composition according to claim 1 which is substantially free of fructose or a fructose containing sacharide.

11. A method of treating a mammal, including man, suffering from a condition mediated through the action of 5 HT at 5 HT$_3$ receptors, which comprises administration of a composition according to claim 1.

12. A method according to claim 11 for the treatment of emesis.

* * * * *